United States Patent [19]

Bennett et al.

[11] Patent Number: 5,374,556

[45] Date of Patent: Dec. 20, 1994

[54] FLEXURE STRUCTURE FOR STAGE POSITIONING

[75] Inventors: Richard R. Bennett; Michael A. Wolf, both of Albuquerque, N. Mex.

[73] Assignee: Cell Robotics, Inc., Albuquerque, N. Mex.

[21] Appl. No.: 919,361

[22] Filed: Jul. 23, 1992

[51] Int. Cl.[5] .............................................. C17M 1/00
[52] U.S. Cl. ................................... 435/287; 435/291; 435/808; 359/392; 248/913; 108/136
[58] Field of Search ............... 435/287, 291, 808, 809; 422/99, 104; 359/391, 392; 248/913, 560, 566, 581, 585, 586, 564; 108/136

[56] References Cited

U.S. PATENT DOCUMENTS

| 500,789 | 7/1893 | Alexander | 108/136 |
|---|---|---|---|
| 2,289,514 | 7/1942 | Mastney et al. | 108/136 |
| 3,006,245 | 10/1961 | Bycer et al. | 359/391 |
| 3,318,593 | 5/1967 | Guernet | 359/392 |
| 3,652,146 | 3/1972 | George | 359/392 |
| 3,704,846 | 12/1972 | Clark | 248/125 |
| 4,209,233 | 6/1980 | Eisler | 359/391 |
| 4,887,721 | 12/1989 | Martin | 209/579 |
| 5,100,627 | 3/1992 | Buican et al. | |
| 5,165,297 | 11/1992 | Krueger | 359/391 |

*Primary Examiner*—William H. Beisner
*Attorney, Agent, or Firm*—Sheldon H. Parker

[57] ABSTRACT

An apparatus for positioning an operational member, particularly for use in an optical laser system for optically trapping and manipulating microscopic particles in a particle manipulation chamber. A flexure member, is provided which has a pair of substantially inflexible parallel members and four sets of flexible spring members. The pair of parallel members is maintained in a spaced relationship by the four sets of flexible spring members. Each of the four sets of flexible members has at least two parallel flexible elements which can be leaf springs or formed as a unitary part of the flexure member. The four sets of flexible spring members are in two groups of two flexible spring members with each of two of groups of flexible members having their two sets of flexible spring members positioned in a "V" shaped pattern. The apices of the "V" shaped patterns are positioned outwardly of each other forming a parallelogram having at least six sides and preferably a parallelogram having eight sides.

37 Claims, 4 Drawing Sheets

FLEXURE STRUCTURE FOR STAGE POSITIONING

FIELD OF THE INVENTION

The instant disclosure relates to an improved mechanism for executing minute adjustments in the position of a stage mechanism, as for example the manipulation chamber of an optical laser trap.

BACKGROUND OF THE PRIOR ART

The physical manipulation of single cells selected on the basis of their individual properties plays an important role in experimental cell biology and immunology, as well as in other areas of biomedical research. Two techniques, flow sorting and micromanipulation, have been used in a wide, albeit mutually exclusive, way for the purposes of cell separation or positioning. Flow sorting allows fast, automated, and essentially nonmechanical separation of cells with given optical and electrical phenotypes. However, both electrostatic and fluidic switching flow sorters divert a volume of fluid containing the cell of interest, rather than the cell itself, and thus, have limited positional accuracy. Micromanipulators can position selected cells with micron accuracy but employ mechanical devices requiring relative large open volumes for unhindered operation.

Optical trapping is a known technique for levitating, positioning and transporting microscopic particles by means of the pressure exerted by one or several laser beams. Particles that can be manipulated by optical trapping include biological cells and cell constituents, such as chromosomes. Optical trapping is particularly important in applications such as the creation of hybrid cell lines, the separation of rare cells, such as fetal cells in maternal blood, and the separation of chromosomes and chromosome fragments.

Optical trapping is based on the transfer of momentum between microscopic particles and the photons they scatter. While the forces produced by this interaction are extremely small, so are the other forces, such as weight and viscous drag, which act on a microscopic particle suspended in a stationary or slowly moving fluid. Optical trap devices are disclosed in U.S. Patents, such as U.S. Pat. Nos. 4,887,721 and 5,100,627.

Under suitable conditions, the interaction between a collimated laser beam and a microscopic particle results in a radial force proportional to the gradient of beam intensity and in the direction of the intensity gradient, and in an axial force proportional to beam intensity and directed along the beam axis. The radial force can act as a restoring force that traps the microscopic particle on the beam axis. In a strongly focused laser beam, as taught in the prior art, the axial force may change sign at a point close to the beam waist, and a full three-dimensional trap results. Short focal length optics are provided and the trap is limited to a small volume close to the focus point. Thus, the particles are trapped about the focus and cannot move along the beam axis for transport. See U.S. Pat. No. 4,887,721, issued Dec. 19, 1989 and U.S. Pat. No. 5,100,627, incorporated herein by reference.

SUMMARY OF THE INVENTION

An apparatus for positioning an operational member along a direction perpendicular to that in which the drive mechanism (e.g. motor and micrometer screw) operates. It has particular utility for positioning the particle manipulation chamber of an optical laser system for optically trapping and manipulating microscopic particles. The flexure mechanism responds to a force applied in the x-y plane to move the manipulation chamber along the z axis. Thus, the drive mechanisms for the x, y and z axes all lie in the x-y plane, providing for a compact configuration of the entire control mechanism. The compact design is particularly critical in optical laser trap devices.

The flexure member has a pair of substantially inflexible parallel members and four sets of flexible spring members. The pair of parallel members is maintained in a spaced relationship by the four sets of flexible spring members. Each of the four sets of flexible members has at least two parallel flexible elements which can be leaf springs or formed as a unitary part of the flexure member. The four sets of flexible spring members are in two groups of two flexible spring members with each of two of groups of flexible members having their two sets of flexible spring members positioned in a "V" shaped pattern.

Each of the leaf springs or flexible spring members of each leg of one of the "V" shaped sets is parallel to the corresponding elements of the diagonally opposite leg of the other of the "V" shaped sets.

The apices (i.e., apexes) of the "V" shaped patterns are positioned outwardly of each other, forming a polygon having at least six sides and preferably having eight sides.

An intermediate member is positioned at the apex of each set of flexible members. One end of each spring is fixed to an intermediate member and the other end of each leaf spring being fixed to one of the pair of parallel members.

A stabilizer means is positioned between the pair of parallel members and has a first end fixed to a first member of the pair of parallel members and a second end fixed to a second member of the pair of parallel members. The stabilizer member is positioned essentially midway between and substantially parallel to the pair of parallel members, such that movement of the pair of parallel members is restricted to movement toward and away from each other, perpendicular to the planes of the parallel members, while the parallel members are maintained in parallel planes.

The flexure member are employed in pairs spaced from and parallel to each other. A frame is employed in combination with the flexure members. The frame has a first and second frame member, each having a first end and a second end. The first flexure member has a first end fixed to a first end of the first frame member and a second end fixed to a second end of the first frame member. The second flexure member has a first end fixed to a first end of the first frame member and a second end fixed to a second end of the second frame member.

BRIEF DESCRIPTION OF THE DRAWINGS

The objects and features of the present invention will more fully become apparent from the following detailed description when taken in connection with the drawings, wherein.

DETAILED DESCRIPTION OF THE INVENTION

Figure 1:
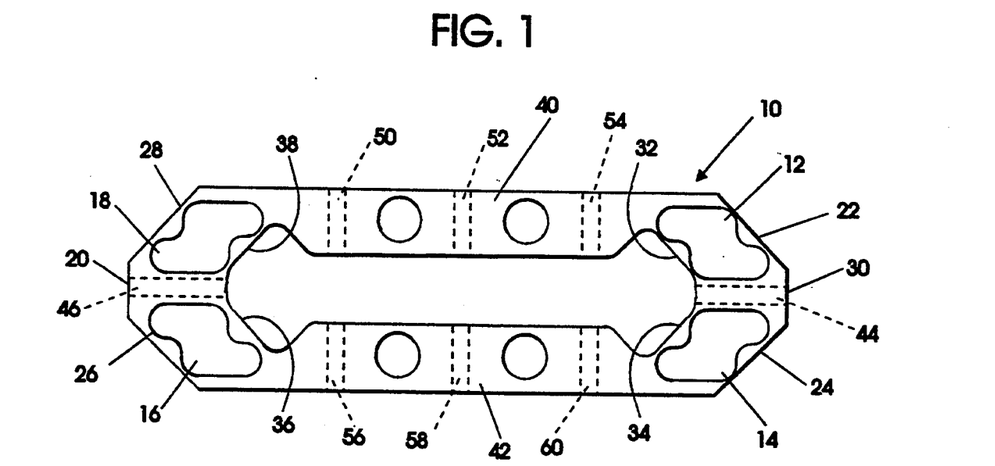
FIG. 1 is a side view of the flexure member of the instant disclosure.

FIG. 1 illustrates the side view of the flexure struture for the positioning of a stage. In a primary application of the flexure member 10 of the instant disclosure, the flexure member is employed to position the manipulation chamber of an optical laser trap. The flexure member 10 responds to a force applied in the x-y plane to move the manipulation chamber along the z axis. Thus, the drive mechanisms for the x, y and z axes all lie in the x-y plane, providing for a compact configuration of the entire control mechanism. The compact design is particularly critical in optical laser trap devices.

The flexure member 10 is an oblong octagon with a hollow center portion. Each of the sides of the octagon is parallel to the opposite side. The top support 40 and bottom support 42 are separated by a leaf spring system which enables minute movement between the top support 40 and bottom support 42. The angled outside walls 22, 24, 26 and 28 are of a sufficient thickness to prevent collapsing but thin enough to allow for the flexing required by the leaf spring system. The interior walls 32, 34, 36 and 38 are parallel to their corresponding angled outside walls with the space between the angled outside walls 22, 24, 26 and 28 and corresponding inside walls 32, 34, 36 and 38 being Z shaped leaf springs 12, 14, 16 and 18. The angled outside walls 22 and 24 and inside walls 32 and 34 are connected by a first support 30. The angled outside walls 26 and 28 and angled inside walls 36 and 38 are connected by a second support 20. The supports 20 and 30 are rigid members and are provided with machined holes 44 and 46. The top support 40 is provided with bolt holes 50, 52 and 54 which are used to secure the top window to the flexure 10. The bottom support 42 is provided with bolt holes 56, 58 and 60 which secure the bottom window to the flexure member 10.

Figure 2:
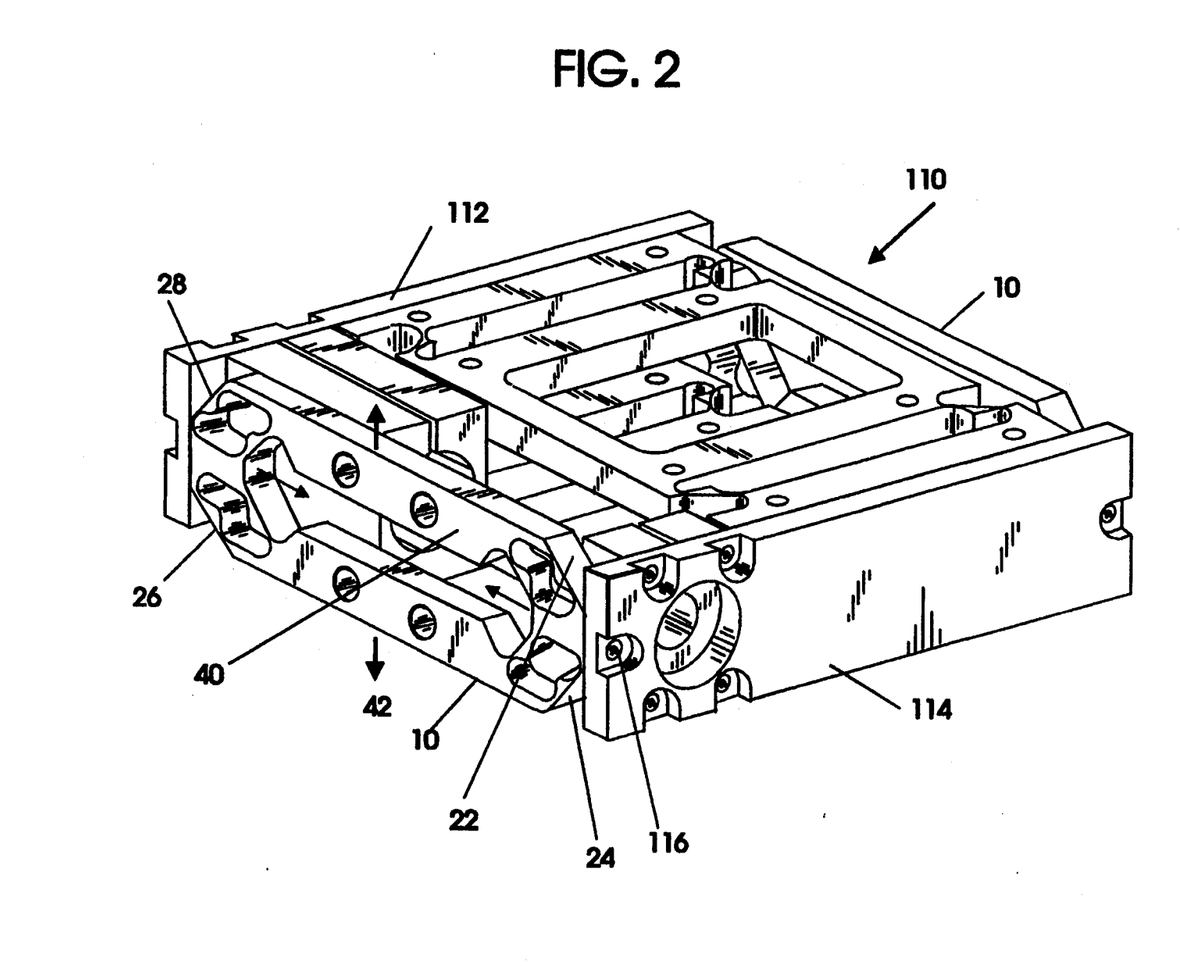
FIG. 2 is a perspective view of the flexure member and stage mechanism of the instant disclosure.

The stage mechanism 110 is illustrated in FIG. 2. The end plates 112 and 114 have been attached to the pair of flexure members 10 through use of bolts or screws. The bolts or screws are placed through receiving holes 116 and 116a (not shown) and secured to the supports 20 and 30 at the machined holes 44 and 46. When external pressure is applied to the end plates 114 and 112, the supports 20 and 30 are forced closer together. The external pressure moves the end plates 112 and 114 in a horizontal direction, which results in the desired motion of the top and bottom of the stage mechanism 110. As the supports 20 and 30 are brought together, the outer angled walls 22, 24, 26 and 28 with their corresponding inside walls 32, 34, 36 and 38, flex, forcing the top support 40 upward and the bottom support 42 downward, relative to the top support.

As an alternative to pressure being applied to the end plates 114 and 112, a bolt or rod is inserted through bolt hole 116, machined holes 44 and 46 and the outer bolt hole. The bolt is secured in place through use of a standard nut. To raise the chamber, the bolt is tightened, forcing the supports 20 and 30 closer together. Alternatively, the bolt can have right hand threads on one half of its length and a left hand thread on its other half. In this manner, rotation of the bolt selectively increases or decreases the distance between the nuts due to the opposed threading of the bolt. While manual adjusting of the pressure on the flexure members is possible, in the application of the flexure member to optical traps, precision servopositioners are necessary to provide minute movement on a highly reproducible basis. The system is readily adaptable to computer control due to its precise and highly reproducible characteristics.

Figure 3:
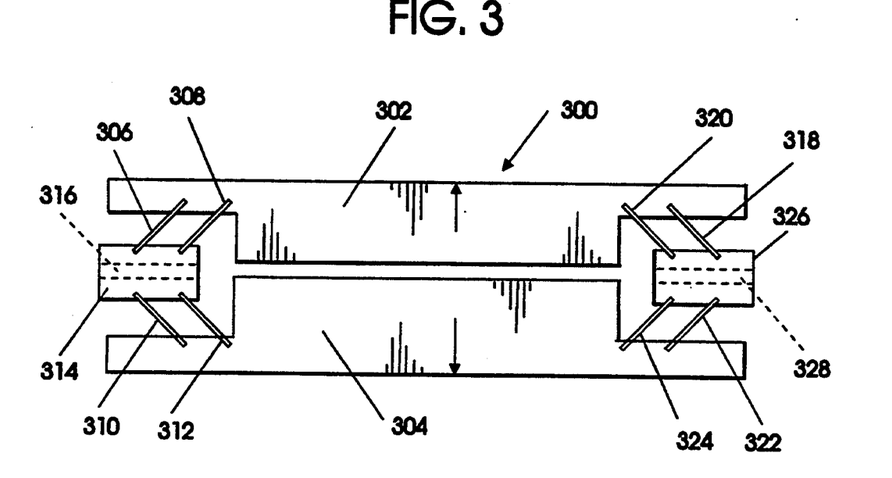
FIG. 3 is a side view of an alternate flexure member of the instant inventions.

FIG. 3 illustrates an alternate flexure member 300 wherein the top support 302 and the bottom support 304 are T shaped members placed with the legs proximate one another. This configuration creates U shaped alcoves at either end of the flexure member 300. Blocks 314 and 326 are placed within the U shaped alcoves with pairs of angled flexures 306, 308, 310, 312, 318, 320, 322 and 324 embedded within. The angled flexures 306, 308, 318, and 320 extend into the top support 302 and the angled flexures 310, 312, 322 and 324 extend into the bottom support 304. The blocks 314 and 326 are provided with screw holes 316 and 328. Pressure is applied to the blocks 314 and 326, forcing the angled flexures 306, 308, 310, 312, 318, 320, 322 and 324 to force the top support 302 and the bottom support 304 to separate.

Figure 4:
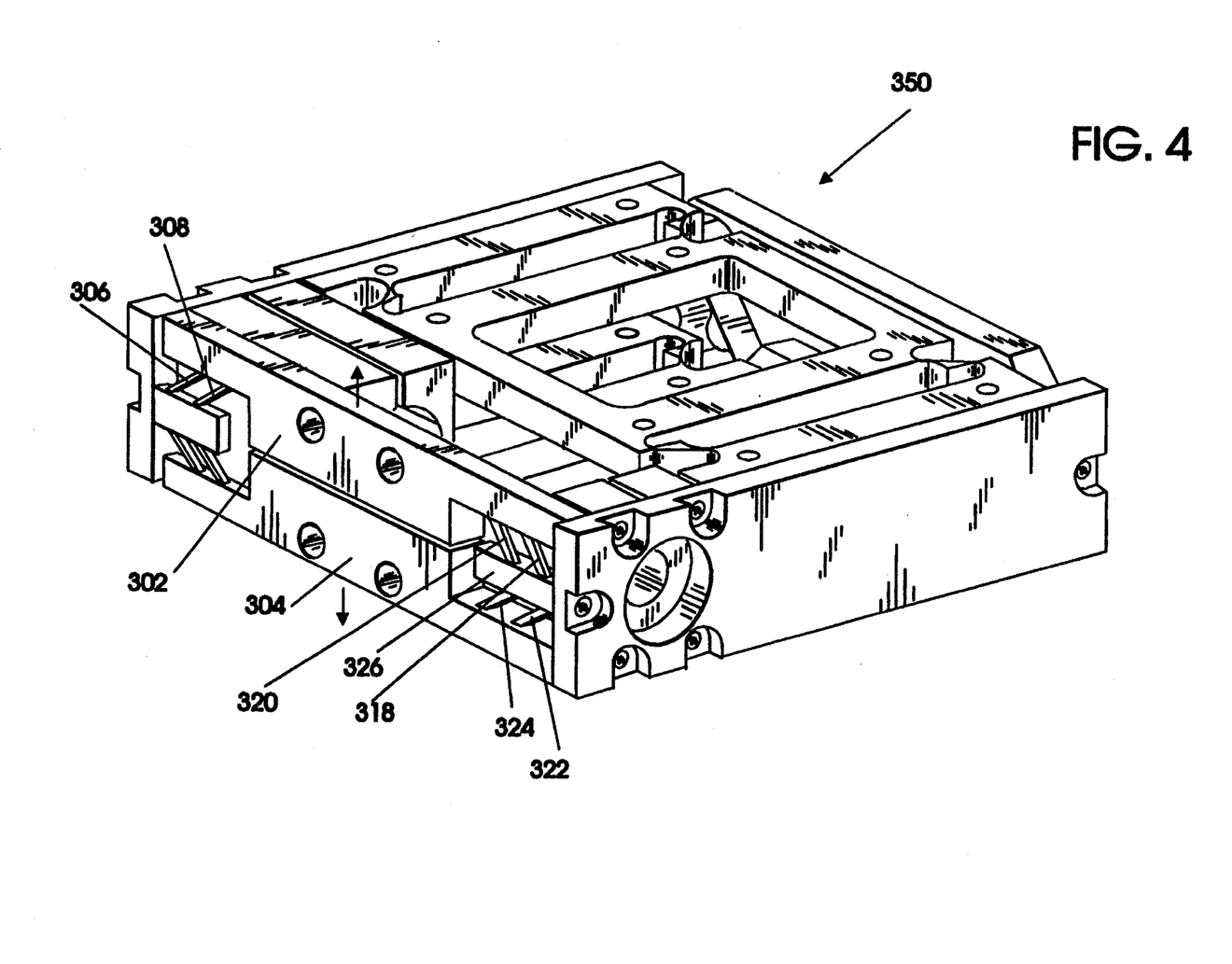
FIG. 4 is a perspective view of the alternative flexure member and the stage mechanism of FIG. 3.

FIG. 4 illustrates a stage mechanism 350 incorporating the alternative flexure member 300. The assembly and operation of the stage mechanism 350 are similar to those described above in the discussion with respect to FIG. 2.

Figure 5:
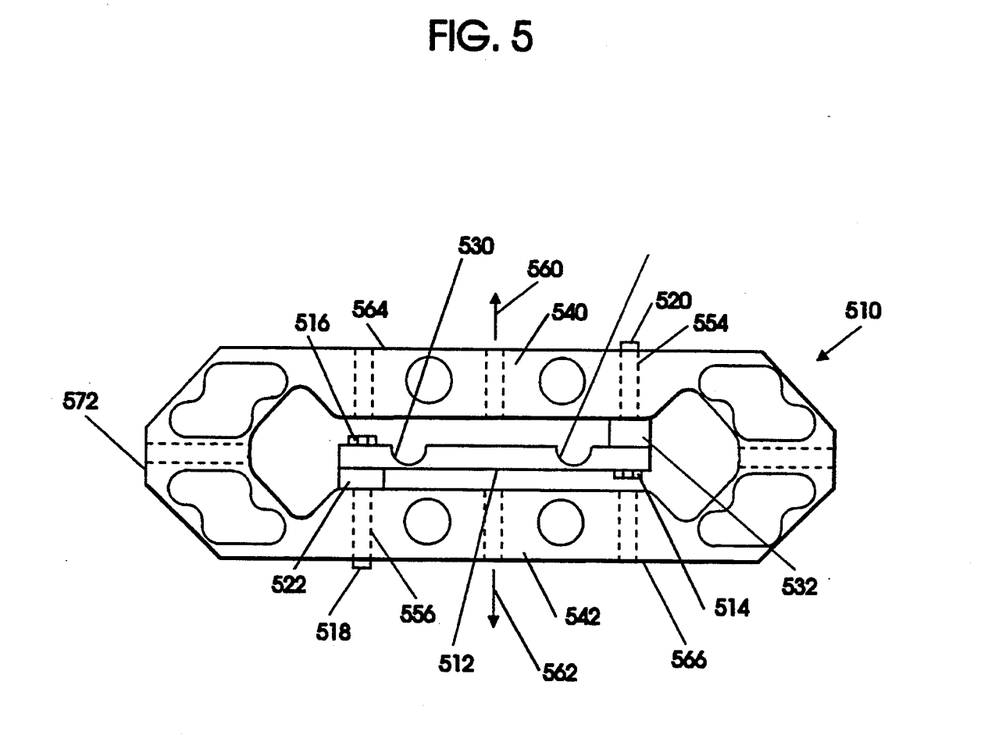
FIG. 5 is a side view of the flexure of FIG. 1 with a stabilizer bar.

FIG. 5 shows the side view of the manipulation chamber flexure member 510 of the instant disclosure. A support bar 512 has been added to the flexure member 510 to provide additional support and prevent the relative lateral movement of the top brace 540 and the bottom brace 542 of flexure member 510. The support bar 512 restricts the relative movement of the top and bottom braces to a movement in the direction of the arrows 560 and 562 rather than a relative "sliding" to the right or left. The support bar 512 is attached to the top support 540 and bottom support 542 through use of nuts 514 and 516 and bolts 518 and 520 or through the use of screws which engage threaded holes. The bolts 518 and 520 are placed through bolt holes 554 and 556. The support bar 512 is spaced from the top support 540 and bottom support 542 by spacers 522 and 524. The spacers 522 and 524 are used to place the support bar 512 midway between the top support 540 and the bottom support 542. The support bar 512 is provided with curvatures 530 and 532 which allow the bar to flex slightly. This flexure allows the top brace 540 and bottom brace 542 to move while preventing sliding. The stabilization provided by the support bar 512 allows the leaf flexure members, as described in FIG. 1, to be of an extremely thin, flexible material which would otherwise lack the structural integrity required for the flexural member.

An example of the specifications of a manipulation chamber, the exterior dimensions would be 240×210×40 mm and the temperature control would range from 10°–40° C. The travel in the horizontal plane (X and Y) is 5 mm with a vertical movement (Z) of 200 $\mu$m.

While the use of the flexure member has been described primarily in its unique association with optical traps, it can have broader applications and can be used wherever precise, minute relative movement of two surfaces is required. It should be noted that the flexure member has a unique ability to maintain its two outer surfaces 564 and 566 in an exact parallel relationship during all phases of the relative movement of the flexure member. Thus, the application of a single force at the outer ends 570 and 572 of the flexure member 510, produces the exact, uniformly parallel movement of the top and bottom braces 540 and 542 of the flexure member.

What is claimed is:

1. A flexure member, comprising:
    a pair of parallel members, said pair of parallel members being substantially parallel and inflexible; and
    four sets of flexible spring members, said four sets of flexible spring members maintaining said pair of parallel members in a spaced parallel relationship, each of said four sets of flexible spring members comprising:
        at least two parallel flexible elements, each of said at least two parallel flexible elements having a first end and a second end,
            said first end of each of said at least two parallel flexible elements being disposed proximate one of said pair of parallel members,
            said second end of each of said at least two parallel flexible members extending diagonally from said one of said pair of parallel members in a direction toward the other of said pair of parallel members,
    wherein said second end of each of said at least two parallel flexible elements of a first set of said four sets of flexible spring members connects with a corresponding second end of said at least two parallel flexible elements of a second set of said four sets of flexible spring members, thereby forming a first vertex and defining an included angle, and,
    wherein said second end of each of said at least two parallel flexible elements of a third set of said four sets of flexible spring members connects with a corresponding second end of said at least two parallel flexible elements of a fourth set of said four sets of flexible spring members, thereby forming a second vertex and defining an included angle;
    wherein said included angle formed at said first vertex and said second vertex is less than 180°.

2. An apparatus for positioning an operational member comprising a flexure member, said flexure member comprising:
    a pair of parallel members, said pair of parallel members being substantially parallel and inflexible, one of said pair of parallel members for supporting said operational member; and
    four sets of flexible spring members, said four sets of flexible spring members maintaining said pair of parallel members in a spaced parallel relationship and responding to an applied force such that said pair of parallel members move toward or away from each other while maintaining said spaced parallel relationship, each of said four sets of flexible spring members comprising:
        at least two parallel flexible elements, each of said at least two parallel flexible elements having a first end and a second end,
            said first end of each of said at least two parallel flexible elements being disposed proximate one of said pair of parallel members,
            said second end of each of said at least two parallel flexible members extending diagonally from said one of said pair of parallel members in a direction toward the other of said pair of parallel members,
    wherein said second end of each of said at least two parallel flexible elements of a first set of said four sets of flexible spring members connects with a corresponding second end of said at least two parallel flexible elements of a second set of said four sets of flexible spring members, thereby forming a first vertex and defining an included angle;
    wherein said second end of each of said at least two parallel flexible elements of a third set of said four sets of flexible spring members connects with a corresponding second end of said at least two parallel flexible elements of a fourth set of said four sets of flexible spring members, thereby forming a second vertex and defining an included angle;
    wherein said included angle formed at said first vertex and said second vertex is less than 180°.

3. The apparatus of claim 2, wherein each of said at least two parallel flexible elements of each of said four sets of flexible spring members comprises a leaf spring.

4. The apparatus of claim 2, wherein said leaf springs of said first set are parallel to said leaf springs of said third set, and said leaf springs of said second set are parallel to said leaf springs of said fourth set.

5. The apparatus of claim 3 wherein, said included angle of said first vertex faces said included angle of said second vertex.

6. The apparatus of claim 5, further comprising a first intermediate member and a second intermediate member, said first intermediate member being positioned at said first vertex and the second intermediate member being positioned at said second vertex, one end of each leaf spring being fixed to one end of said pair of parallel members.

7. The apparatus of claim 6, further comprising stabilizer means, said stabilizer means being positioned between said pair of parallel members, said parallel members being disposed to lie within the same plane, said stabilizer means having a first end fixed to one of said pair of parallel members and a second end fixed to the other of said pair of parallel members, said stabilizer means being positioned essentially midway between and substantially parallel to said pair of parallel members, whereby movement of said pair of parallel members is restricted to movement toward and away from each other within said same plane.

8. The apparatus of claim 2, wherein said flexure member is a unitary element.

9. The apparatus of claim 8, wherein each of said at least two flexible elements of each set of said four sets of flexible spring members is a spring element capable of leaf spring flexure.

10. The apparatus of claim 9, wherein said included angle of said first vertex faces said included angle of said second vertex.

11. The apparatus of claim 10, wherein said spring elements capable of leaf spring flexure of said first set are parallel to said spring elements capable of leaf spring flexure of said third set, and said spring elements capable of leaf spring flexure of said second set are parallel to said spring elements capable of leaf spring flexure of said fourth set.

12. The apparatus of claim 11, further comprising a first and a second intermediate member, said first intermediate member being positioned at said first vertex and the second intermediate member being positioned at said second vertex, one end of each spring element being fixed to an intermediate member and the other end of each spring element being fixed to one of said pair of parallel members.

13. The apparatus of claim 10, further comprising stabilizer means, said stabilizer means being positioned between said pair of parallel members, said parallel members being disposed to lie within the same plane, said stabilizer means having a first end fixed to one of said pair of parallel members and a second end fixed to the other of said pair of parallel members, said stabilizer means being positioned essentially midway between and substantially parallel to said pair of parallel members, whereby movement of said pair of parallel members is restricted to movement toward and away from each other within said same plane.

14. The apparatus of claim 11, wherein each of said spring elements capable of leaf spring flexure has at least two primary regions of flexure along its length.

15. The apparatus of claim 8, wherein said flexure member is a polygon having at least six sides.

16. The apparatus of claim 15, wherein said flexure member is a polygon having eight sides.

17. An apparatus for positioning an operational member comprising a first and a second flexure member, each said flexure member comprising:
   a. a pair of parallel members, said pair of parallel members being substantially parallel and inflexible, one of said pair of parallel members for supporting said operational member
   b. four sets of flexible spring members, said four sets of flexible spring members maintaining said pair of parallel members in a spaced parallel relationship and responding to an applied force such that said pair of parallel members move toward or away from each other while maintaining said spaced parallel relationship, each of said four sets of flexible spring members comprising:
      at least two parallel flexible elements, each of said at least two parallel flexible elements having a first end and a second end,
         said first end of each of said at least two parallel flexible elements being disposed proximate one of said pair of parallel members,
         said second end of each of said at least two parallel flexible members extending diagonally from said one of said pair of parallel members in a direction toward the other of said pair of parallel members,
      wherein said second end of each of said at least two parallel flexible elements of a first set of said four sets of flexible spring members connects with a corresponding second end of said at least two parallel flexible elements of a second set of said four sets of flexible spring members, thereby forming a first vertex and defining an included angle;
      wherein said second end of each of said at least two parallel flexible elements of a third set of said four sets of flexible spring members connects with a corresponding second end of said at least two parallel flexible elements of a fourth set of said four sets of flexible spring members, thereby forming a second vertex and defining an included angle;
      wherein said included angle formed at said first vertex and said second vertex is less than 180°,
   said first flexure member being spaced from and parallel to said second flexure member, and frame means, said frame means having a first and second frame member, each of said first and second frame members having a first end and a second end, said first vertex of said first flexure member being fixed to said first end of said first frame member and said second vertex of said first flexure member being fixed to said first end of said second frame member, said first vertex of said second flexure member being fixed to said second end of said first frame member and said second vertex of said second flexure member being fixed to said second end of said second frame member, wherein said frame means simultaneously applies an external force to said first and second flexure members.

18. The apparatus of claim 17, wherein each said flexure member is a unitary element.

19. The apparatus of claim 18, wherein in each said flexure member each of said at least two flexible elements of each set of said four sets of flexible spring members comprise a spring elements capable of leaf spring flexure.

20. The apparatus of claim 19, wherein in each said flexure member, said included angle of said first vertex faces said included angle of said second vertex.

21. The apparatus of claim 20, wherein in each said flexure member, said spring elements capable of leaf spring flexure of said first set are parallel to said spring elements capable of leaf spring flexure of said third set, and said spring elements capable of leaf spring flexure of said second set are parallel to said spring elements capable of leaf spring flexure of said fourth set.

22. The apparatus of claim 21, wherein each said flexure member further comprises a first and a second intermediate member, said first intermediate member being positioned at said first vertex and the second intermediate member being positioned at said second vertex, one end of each spring element being fixed to an intermediate member and the other end of each spring element being fixed to one of said pair of parallel members.

23. The apparatus of claim 20, wherein each said flexure member further comprises stabilizer means, said stabilizer means being positioned between said pair of parallel members, said parallel members being disposed to lie within the same plane, said stabilizer means having a first end fixed to one of said pair of parallel members and a second end fixed to the other of said pair of parallel members, said stabilizer means being positioned essentially midway between and substantially parallel to said pair of parallel members, whereby movement of said pair of parallel members is restricted to movement toward and away from each other within said same planes.

24. The apparatus of claim 21, wherein each of said spring elements capable of leaf spring flexure has at least two primary regions of flexure along its length.

25. The apparatus of claim 18, wherein each said flexure member is a polygon having at least six sides.

26. The apparatus of claim 25, wherein each said flexure member is a polygon having eight sides.

27. In a laser system for optically trapping and manipulating microscopic particles in a particle manipulation chamber the improvement comprising means for positioning said particle manipulation chamber, said means including a flexure member, said flexure member comprising:
   a. a pair of parallel members, said pair of parallel members being substantially parallel and inflexible, one of said pair of parallel members for supporting said particle manipulation chamber, b. four sets of flexible spring members, said four sets of flexible spring members maintaining said pair of parallel members in a spaced parallel relationship and responding to an applied force such that said pair of parallel members move toward or away from each other while maintaining said spaced parallel relationship, each of said four sets of flexible spring members comprising:

at least two parallel flexible elements, each of said at least two parallel flexible elements having a first end and a second end, said first end of each of said at least two parallel flexible elements being disposed proximate one of said pair of parallel members, said second end of each of said at least two parallel flexible members extending diagonally from said one of said pair of parallel members in a direction toward the other of said pair of parallel members, wherein said second end of each of said at least two parallel flexible elements of a first set of said four sets of flexible spring members connects with a corresponding second end of said at least two parallel flexible elements of a second set of said four sets of flexible spring members, thereby forming a first vertex and defining an included angle;

wherein said second end of each of said at least two parallel flexible elements of a third set of said four sets of flexible spring members connects with a corresponding second end of said at least two parallel flexible elements of a fourth set of said four sets of flexible spring members, thereby forming a second vertex and defining an included angle;

wherein said included angle formed at said first vertex and said second vertex is less than 180°.

28. The apparatus of claim 27, wherein said means for positioning said particle manipulation chamber further comprises a second flexure member, said second flexure member comprising:

a. a pair of parallel members, said pair of parallel members being substantially parallel and inflexible, one of said pair of parallel members for supporting said manipulation chamber, b. four sets of flexible spring members, said four sets of flexible spring members maintaining said pair of parallel members in a spaced parallel relationship and responding to an applied force such that said pair of parallel members move toward or away from each other while maintaining said spaced parallel relationship, each of said four sets of flexible spring members comprising:

at least two parallel flexible elements, each of said at least two parallel flexible elements having a first end and a second end, said first end of each of said at least two parallel flexible elements being disposed proximate one of said pair of parallel members, said second end of each of said at least two parallel flexible members extending diagonally from said one of said pair of parallel members in a direction toward the other of said pair of parallel members, wherein said second end of each of said at least two parallel flexible elements of a first set of said four sets of flexible spring members connects with a corresponding second end of said at least two parallel flexible elements of a second set of said four sets of flexible spring members, thereby forming a first vertex and defining an included angle;

wherein said second end of each of said at least two parallel flexible elements of a third set of said four sets of flexible spring members connects with a corresponding second end of said at least two parallel flexible elements of a fourth set of said four sets of flexible spring members, thereby forming a second vertex and defining an included angle;

wherein said included angle formed at said first vertex and said second vertex is less than 180°, said first flexure member being spaced from and parallel to said second flexure member, and frame means, said frame means having a first and second frame member, each of said first and second frame members having a first end and a second end, said first vertex of said first flexure member being fixed to said first end of said first frame member and said second vertex of said first flexure member being fixed to said first end of said second frame member, said first vertex of said second flexure member being fixed to said second end of said first frame member and said second vertex of said second flexure member being fixed to said second end of said second frame member, wherein said frame means simultaneously applies an external force to said first and second flexure members.

29. The apparatus of claim 28, wherein each said flexure member is a unitary element.

30. The apparatus of claim 29, wherein in each said flexure member, each of said at least two flexible elements of each set of said four sets of flexible spring members is a spring element capable of leaf spring flexure.

31. The apparatus of claim 30, wherein in each said flexure member, said included angle of said first vertex faces said included angle of said second vertex.

32. The apparatus of claim 31, wherein in each said flexure member, said spring elements capable of leaf spring flexure of said first set are parallel to said spring elements capable of leaf spring flexure of said third set, and said spring elements capable of leaf spring flexure of said second set are parallel to said spring elements capable of leaf spring flexure of said fourth set.

33. The apparatus of claim 32, wherein each said flexure member further comprises a first and a second intermediate member, said first intermediate member being positioned at said first vertex and the second intermediate member being positioned at said second vertex, one end of each spring element being fixed to an intermediate member and the other end of each spring element being fixed to one of said pair of parallel members.

34. The apparatus of claim 33, wherein each said flexure member further comprises stabilizer means, said stabilizer means being positioned between said pair of parallel members, said parallel members being disposed to lie within the same plane, said stabilizer means having a first end fixed to one of said pair of parallel members and a second end fixed to the other of said pair of parallel members, said stabilizer means being positioned essentially midway between and substantially parallel to said pair of parallel members, whereby movement of said pair of parallel members is restricted to movement toward and away from each other within said same plane.

35. The apparatus of claim 33, wherein each of said spring elements capable of leaf spring flexure has at least two primary regions of flexure along its length.

36. The apparatus of claim 35, wherein each said flexure member is a polygon having at least six sides.

37. The apparatus of claim 36, wherein each said flexure member is a polygon having eight sides.

* * * * *